(12) United States Patent
Shinbata

(10) Patent No.: US 6,678,400 B1
(45) Date of Patent: Jan. 13, 2004

(54) IMAGE PROCESSING APPARATUS, METHOD AND MEMORY MEDIUM

(75) Inventor: Hiroyuki Shinbata, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/557,316

(22) Filed: Apr. 25, 2000

(30) Foreign Application Priority Data

Apr. 30, 1999 (JP) ............................................ 11-124749

(51) Int. Cl.[7] ................................................. G06K 9/00
(52) U.S. Cl. ........................................ 382/132; 128/922
(58) Field of Search ............................... 382/274, 132, 382/260, 275, 263, 266, 254, 128, 129, 130, 131; 348/687; 324/307; 358/3.26, 3.27; 128/922

(56) References Cited

U.S. PATENT DOCUMENTS

| | | | | |
|---|---|---|---|---|
| 4,315,318 A | * | 2/1982 | Kato et al. ................ | 382/264 |
| 4,346,409 A | * | 8/1982 | Ishida et al. ............... | 358/461 |
| 4,731,865 A | * | 3/1988 | Sievenpiper ............... | 382/274 |
| 5,319,719 A | * | 6/1994 | Nakazawa et al. .......... | 382/132 |
| 5,369,572 A | * | 11/1994 | Haraki et al. .............. | 378/83 |
| 5,454,044 A | * | 9/1995 | Nakajima .................. | 382/132 |
| 5,493,622 A | * | 2/1996 | Tsuchino et al. ........... | 382/132 |
| 6,269,176 B1 | * | 7/2001 | Barski et al. .............. | 382/128 |
| 6,480,300 B1 | * | 11/2002 | Aoyama .................... | 358/1.9 |

FOREIGN PATENT DOCUMENTS

| | | |
|---|---|---|
| JP | 6-46409 | 6/1994 |
| JP | 2509503 | 4/1996 |
| JP | 2663189 | 6/1997 |

OTHER PUBLICATIONS

Anan et al., Journal of Japanese Society of Radiological Tech., vol. 45, No. 8, Aug., 1989, p. 1030.

* cited by examiner

Primary Examiner—Jayanti K. Patel
Assistant Examiner—Seyed Azarian
(74) Attorney, Agent, or Firm—Fitzpatrick, Cella, Harper & Scinto

(57) ABSTRACT

There is disclosed an image processing apparatus for performing a dynamic range compression processing to an arbitrary image to add a high frequency component obtained based on the image, the image processing apparatus comprising: conversion means for converting the magnitude of the amplitude of the added high frequency component based on the magnitude of the high frequency component. When the dynamic range compression processing is performed, artifacts such as an overshoot and undershoot are depressed, the amplitude of the high frequency component is held and the width of an image density distribution is set to be freely adjustable, so that a satisfactory processed image can be obtained.

2 Claims, 9 Drawing Sheets

IMAGE PROCESSING APPARATUS, METHOD AND MEMORY MEDIUM

BACKGROUND OF THE INVENTION

1. Field of the Invention

The present invention relates to an image processing apparatus for performing an image processing, for example, including a dynamic range compression processing for adding a high frequency component of an original image to the original image (dynamic range change processing), an image processing system, an image processing method, and a memory medium for storing processing steps to perform the processing in a computer readable manner.

2. Related Background Art

In recent years, with an advancement of digital technique, for example, a method is executed which comprises: digitizing a photographed image obtained by X-ray photographing (hereinafter also referred to as "X-ray image"), performing an image processing to the digitized image; and displaying the image on a monitor apparatus, or outputting the image onto an X-ray diagnosis film.

Here, the X-ray image is constituted of an image area in which it is easy to transmit X-rays, and an image area in which it is very difficult to transmit the X-rays. For example, the X-ray image of a chest (lungs) is constituted of a lung image area in which it is easy to transmit the X-rays, and a mediastinum image area in which it is very difficult to transmit the X-rays. In this manner, since the dynamic range in which pixel values are present (hereinafter also referred to as "density range") is much broadened in the X-ray image, it has been difficult to obtain an X-ray image in which both the lung and mediastinum image areas far different in X-ray transmittance from each other can simultaneously be observed.

Therefore, in order to avoid the above-described problem, the following methods 1 to 5 of a dynamic range compression processing (hereinafter also referred to as "DRC processing") have been proposed.

Method 1:

In method 1 described in "SPIE Vol. 626 Medicine XIV/PACSIV (1986)" or the like, assuming that the pixel value of the processed image is "$S_D$", the pixel value of the original image (input original image) is "$S_{org}$", and the pixel value of the low frequency component of the original image (pixel value of a smoothed image) is "$S_{US}$", equation (1) is represented with constants A, B, C (e.g., A=3, B=0.7).

$$S_D = A[S_{org} - S_{US}] + B[S_{US}] + C \quad (1)$$

Moreover, in the method 1, by changing weighting (constants A and B) of the high frequency component (first term) and low frequency component (second term) in the equation (1) and, for example, assuming A=3, B=0.7, the high frequency component is emphasized, and the dynamic range of the entire image can be compressed. This is evaluated by many radiotherapists, et al. such that the image subjected to the present processing is effective for diagnosis as compared with the image not subjected to the present processing.

Method 2:

In a method 2 described in Japanese Patent Publication No. 6-046409, assuming that the pixel value of the processed image is "$S_D$", the pixel value of the original image is "$S_{org}$", and the pixel value of the low frequency component of the original image (pixel value of the smoothed image) is "$S_{US}$", equation (2) is represented with a monotonous decrease function f(X).

$$S_D = S_{org} + f(S_{US}) \quad (2)$$

Also in this method 2, similarly to the above-described method 1, the dynamic range of the entire image can be compressed based on the low frequency component of the original image.

Method 3:

In a method 3 described in Japanese Patent No. 2509503, assuming that the pixel value of the processed image is "$S_D$", and the pixel value of the original image is "$S_{org}$", equation (3) is represented with the average profile Py of the Y-directional profile of the original image, and the average profile Px of the X-directional profile.

$$S_D = S_{org} + F[G(Px, Py)] \quad (3)$$

Here, the property of the function F(x) in the equation (3) will be described. First, in "x>Dth", F(0) is "0". Moreover, in "0≦x≦Dth", F(x) monotonously decreases with an intercept "E", and inclination "E/Dth", and is represented by equation (4).

$$F[x] = E - (E/Dth)X \quad (4)$$

Moreover, the average profiles Py and Px in the equation (3) are represented by equations (5) and (6) with profiles pyi and pxi (i=1 to n).

$$Py = (\Sigma Pyi)/n \quad (5)$$

$$Px = (\Sigma Pxi)/n \quad (6)$$

Moreover, "G(Px,Py)" in the equation (3) is represented by equation (7).

$$G(Px, Py) = \max(px, py) \quad (7)$$

Therefore, in the method 3, the dynamic range is compressed when the pixel value of the low frequency component is Dth or less.

Method 4:

A method 4 similar to the method 2 described in the Japanese Patent Publication No. 6-046409 and the method 3 described in the Japanese Patent No. 2509503 is described in "Journal of Japanese Society of Radiological Technology, Vol. 45, No. 8, August, 1989, p. 1030, Anan et al".

Assuming that the pixel value of the processed image is "$S_D$", the pixel value of the original image is "$S_{org}$", and the average pixel value (pixel value of the smoothed image) obtained by taking the moving average of the original image with a mask size of M×M pixels is "$S_{US}$", the method 4 is represented by equations (8) and (9) with the monotonous decrease function f(X).

$$S_D = S_{org} + f(S_{US}) \quad (8)$$

$$S_{US} = \Sigma S_{org}/M^2 \quad (9)$$

Moreover, the equation (8) can be changed to equation (10).

$$S_D = (S_{org} - S_{US}) + (f(S_{US}) + S_{US}) \quad (10)$$
$$= (S_{org} - S_{US}) + f1(S_{US})$$

Here, the method 4 is different from the method 3 represented by the equation (3) in method of generating the low frequency component, the low frequency component is generated with one-dimensional data in the method 3, and the low frequency component is generated by two-dimensional data in the method 4.

Also in the method 4, similarly to the above-described method 3, the dynamic range is compressed when the pixel value of the low frequency component is Dth or less.

Method 5:

For a method 5 described in Japanese Patent No. 2663189, assuming that the pixel value of the processed image is "$S_D$", the pixel value of the original image is "$S_{org}$", and the average pixel value (pixel value of the smoothed image) obtained by taking the moving average of the original image with the mask size of M×M pixels is "$S_{US}$" equations (11) and (12) are represented with the monotonous decrease function f2(X).

$$S_D = S_{org} + f2(S_{US}) \quad (11)$$
$$= (S_{org} - S_{US}) + f3(S_{US})$$
$$f3(S_{US}) = f2(S_{US}) + S_{US}$$

$$S_{US} = \sum S_{org}/M^2 \quad (12)$$

Here, the property of the function f2(x) in the equation (11) will be described. First, in "x<Dth", f2(0) is "0". Moreover, in "Dth≦x", f2(x) monotonously decreases with the intercept "E", and inclination "E/Dth", and is represented by equation (13).

$$f2[x]=E-(E/Dth)X \quad (13)$$

Therefore, in the method 5, the dynamic range is compressed when the low frequency component pixel value is Dth or less.

Additionally, the compression algorithm of the dynamic range in the method 5 is similar to the algorithm in the method 4 described in the "Journal of Japanese Society of Radiological Technology, Vol. 45, No. 8, August, 1989, p. 1030, Anan et al".

However, the conventional image processing method using the above-described methods 1 to 5 of the DRC processing has at least the following problems 1 and 2.

Problem 1:

For example, as shown in FIG. 14, when the original image (input original image) is subjected to the DRC processing represented by the "Journal of Japanese Society of Radiological Technology, Vol. 45, No. 8, August, 1989, p. 1030, Anan et al.", particularly to the DRC processing including the processing (original image—smoothed image) of subtracting the pixel value $S_{US}$ of the smoothed image from the pixel value $S_{org}$ of the original image as shown in the equations (10) and (11), artifacts called overshoot and undershoot are generated in the edge part of the inputted original image.

Concretely, first the cause of the overshoot and undershoot will be described with reference to FIGS. 15A, 15B and 15C.

In FIGS. 15A, 15B and 15C, solid lines show image profiles, and broken lines show coordinates. Moreover, FIG. 15A shows the profile of the edge part of the original image, FIG. 15B shows the profile of the image (smoothed image) obtained by smoothing the original image, and FIG. 15C shows the profile of the image (corresponding to the image of the high frequency component) obtained after subtracting the smoothed image shown in FIG. 15B from the original image shown in FIG. 15A.

As shown in FIG. 15C, when the original image is smoothed, the shape of the original image profile is not stored in the edge part. This causes the overshoot and undershoot.

On the other hand, in FIG. 14, the abscissa indicates an image coordinate, and the ordinate indicates an image pixel value. Moreover, in FIG. 14, (A) shows an original image profile. Here, the original image is a step-shaped image in which the pixel value increases by 450 at each 300 pixels, or an image in which the pixel value of 50 as the high frequency component is added to every 50 pixels. Moreover, in FIG. 14, (B) shows the profile of the image obtained by performing the conventional DRC processing to the original image.

Therefore, as apparent from (B) of FIG. 14, since the conventional DRC processing includes a processing of subtracting the smoothed image ($S_{US}$) of the original image from the original image ($S_{org}$) to extract the high frequency component, for the reason described with reference to FIG. 15, the artifacts (overshoot and undershoot) are generated in the edge part of the original image.

Problem 2:

The object of the DRC processing by the above-described methods 1 and 2 is to compress the dynamic range of the pixel values of the object area in the image and obtain the image in which the entire object area can simultaneously be observed.

Therefore, for example, for the lung X-ray image, by compressing the dynamic range of the mediastinum area with a low density in the lung and mediastinum image areas constituting the lung area, it is possible to obtain the image in which both the lung and mediastinum image areas can simultaneously be observed. This is because the density of the low-density side image area is raised to a visible area by compressing the dynamic range of the low-density side image area which is not included in the visible area.

However, in the X-ray image, the low-density side image area of the object area is very low in X-ray transmittance, and usually the S/N ratio also tends to be low as compared with the (high-density side) area high in X-ray transmittance. Therefore, noises are sometimes conspicuous at a certain pixel value or less. In this case, even when the pixel value of the low-density side image area is raised to the visible area by the DRC processing, there is a problem that the effective information of the object area, particularly the information of the low frequency component such as density distribution is obstructed by the noises and cannot easily be observed.

SUMMARY OF THE INVENTION

Therefore, the present invention has been developed to remove the above-described disadvantages, and an object thereof is to provide an image processing apparatus in which when a dynamic range compression processing is performed, artifacts such as an overshoot and undershoot are depressed, the amplitude of an image high frequency component is held and the width of an image density distribution is set to be freely adjustable, so that a satisfactory processed image can be obtained, an image processing system, an image processing method, and a memory medium for storing process steps to perform the processing in a computer readable manner.

To attain the object, according to the present invention, there is provided an image processing apparatus for performing a dynamic range compression processing to an arbitrary image to add a high frequency component obtained based on the image, and the image processing apparatus comprises conversion means for converting the magnitude of the amplitude of the added high frequency component based on the magnitude of the high frequency component.

Other objects and characteristics of the present invention will be apparent from the following description and drawings.

DETAILED DESCRIPTION OF THE PREFERRED EMBODIMENTS

Embodiments of the present invention will be described hereinafter with reference to the drawings.

First Embodiment

Figure 1:
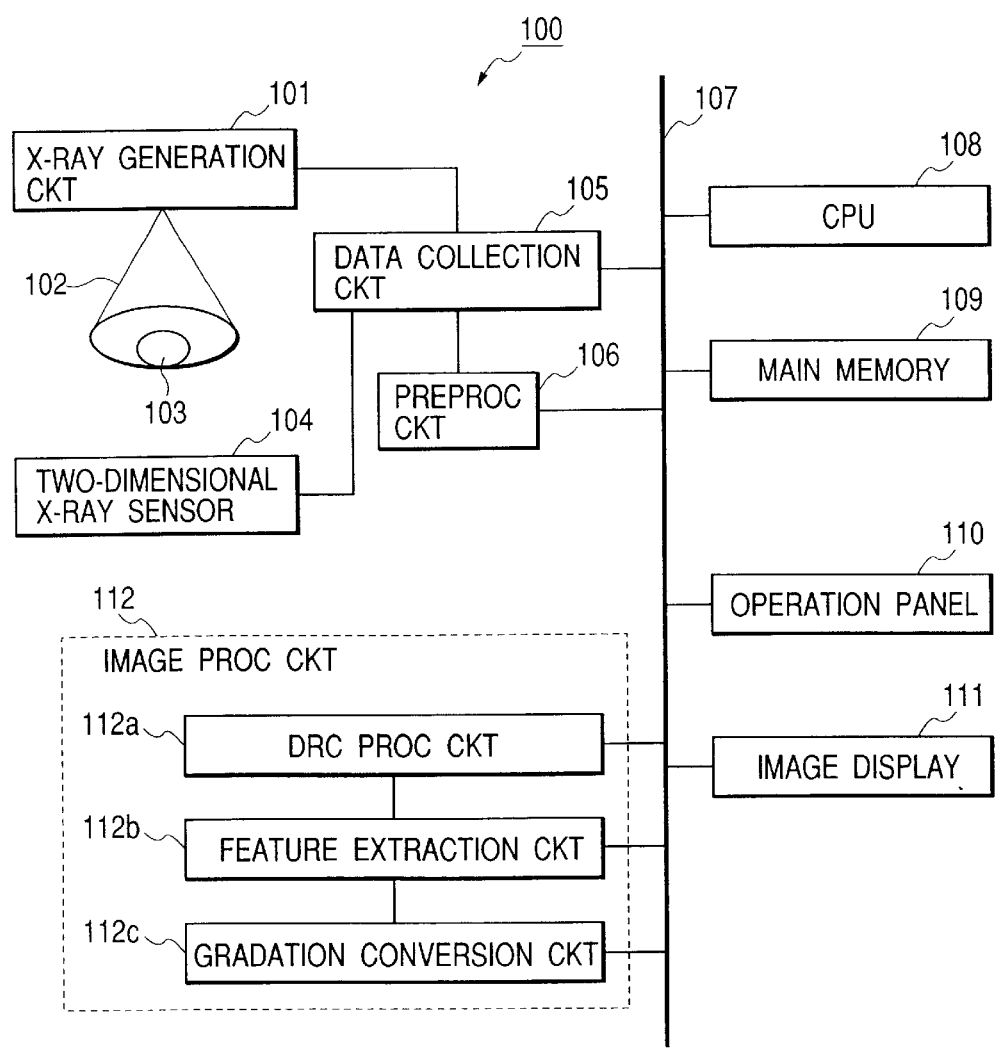
FIG. 1 is a block diagram showing the constitution of an X-ray photographing apparatus to which the present invention is applied.

The present invention is applied, for example, to an X-ray photographing apparatus 100 shown in FIG. 1.

This X-ray photographing apparatus 100 has an image processing function including a dynamic range compression processing (DRC processing) and, as shown in FIG. 1, comprises: an X-ray generation circuit 101 for generating X-rays; a two-dimensional X-ray sensor 104 in which the X-ray transmitted through an object 103 forms an image; a data collection circuit 105 for collecting photographed images outputted from the two-dimensional X-ray sensor 104; a preprocessing circuit 106 for performing a preprocessing to the photographed image collected by the data collection circuit 105; a main memory 109 for storing various information of the photographed image (original image) subjected to the preprocessing in the preprocessing circuit 106 and a processing program for executing various processings; an operation panel 110 for performing instructions for execution of X-ray photographing, and the like and various settings to the present apparatus; an image processing circuit 112 for performing an image processing including the DRC processing to the photographed image (original image) subjected to the preprocessing in the preprocessing circuit 106; an image display 111 for displaying the processed images of the image processing circuit 112; and CPU 108 for controlling the entire operation of the present apparatus. The data collection circuit 105, preprocessing circuit 106, image processing circuit 112, CPU 108, main memory 109, operation panel 110, and image display 111 are connected to a CPU bus 107 to transmit/receive data with one another.

Moreover, the image processing circuit 112 includes a DRC processing circuit 112a for performing the DRC processing to the original image, a feature extraction circuit 112b for extracting a feature amount from the original image, and a gradation conversion circuit 112c for performing a gradation conversion processing to the processed image of the DRC processing circuit 112a based on the feature amount obtained by the feature extraction circuit 112b.

Here, the DRC processing circuit 112a is constituted to convert the high frequency component in accordance with a high frequency component amplitude when the image high frequency component is added to the original image or the image obtained by smoothing the original image, and constitutes the most characteristic part of the present embodiment.

Figure 2:
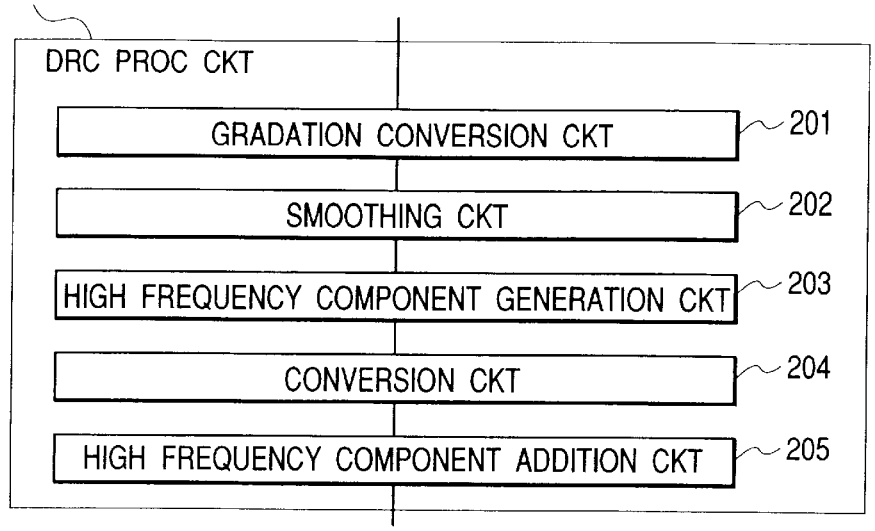
FIG. 2 is a block diagram showing the constitution of a dynamic range compression processing circuit of the X-ray photographing apparatus in a first embodiment.

Therefore, for example, as shown in FIG. 2, the DRC processing circuit 112a includes a gradation conversion circuit 201 for gradation-converting an original image density, a smoothing circuit 202 for smoothing the processed image of the gradation conversion circuit 201, a high frequency component generation circuit 203 for subtracting the smoothed image obtained in the smoothing circuit 202 from the processed image of the gradation conversion circuit 201 to obtain the high frequency component of the image, a conversion circuit 204 for converting the amplitude of the high frequency component obtained by the high frequency component generation circuit 203, and a high frequency component addition circuit 205 for adding the high frequency component converted by the conversion circuit 204 to the processed image of the gradation conversion circuit 201.

Figure 3:
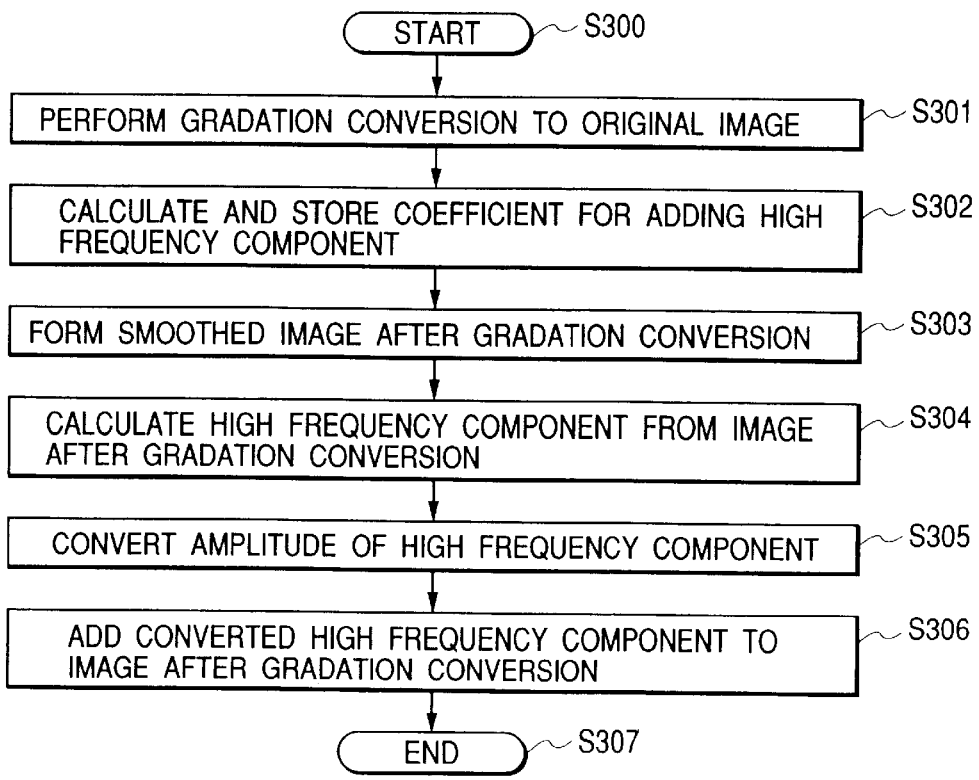
FIG. 3 is a flowchart showing the operation of the dynamic range compression processing circuit.

Moreover, in the above-described X-ray photographing apparatus 100, first the main memory 109 pre-stores the data necessary for executing various processings in the CPU 108, processing program, and the like, and further includes a work memory for the operation of the CPU 108. As the processing program stored in the main memory 109, particularly as the processing program for the DRC processing, for example, the processing program according to a flowchart of FIG. 3 is used here.

Therefore, by reading and executing the above-described processing program, and the like from the main memory 109, the CPU 108 controls the entire operation of the present apparatus according to the operation from the operation panel 110 as described later.

Step S300:

First, the X-ray generation circuit 101 radiates an X-ray beam 102 to a test object 103. The X-ray beam 102 radiated from the X-ray generation circuit 101 is attenuated and transmitted through the test object 103, reaches the two-dimensional X-ray sensor 104, and is outputted as an X-ray image from the two-dimensional X-ray sensor 104. Here, the X-ray image outputted from the two-dimensional X-ray sensor 104 is used, for example, as a lung X-ray image 300 constituted of a lung field and mediastinum.

Subsequently, the data collection circuit 105 converts the X-ray image outputted from the two-dimensional X-ray sensor 104 to an electric signal, and supplies the signal to the preprocessing circuit 106.

The preprocessing circuit 106 performs preprocessings such as an offset correction processing and a gain correction processing to the signal (X-ray image signal) from the data collection circuit 105. The X-ray image signal subjected to the preprocessing in the preprocessing circuit 106 is transferred as input image information to the main memory 109 and image processing circuit 112 via the CPU bus 107 by the control of the CPU 108.

Subsequently, the DRC processing circuit 112a of the image processing circuit 112 executes the processing of the following steps S301 to S306.

Figure 4:
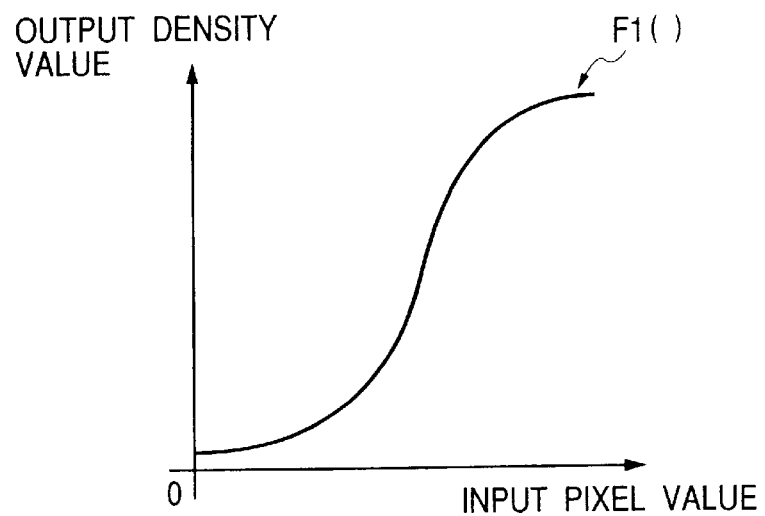
FIG. 4 is a diagram showing one example of a gradation conversion curve for use in the gradation conversion circuit of the dynamic range compression processing circuit.

Step S301:

First, the gradation conversion circuit 201 uses, for example, a gradation conversion curve F1( ) shown in FIG. 4 to perform a gradation conversion processing shown in equation (14) to the image (original image) transferred via the CPU bus 107.

$$f0(x,y)=F1(f1(x,y)) \qquad (14)$$

In the equation (14), "f1(x,y)" indicates the pixel value of the original image (two-dimensional original image) which is a processing object, and "x" and "y" indicate two-dimensional X and Y coordinates of the original image. Moreover, "f0(x,y)" indicates the pixel value of the original image (output image) after the gradation conversion processing.

Additionally, the gradation conversion curve F1( ) shown in FIG. 4 is an example of the gradation conversion curve for use in the gradation conversion circuit 201, and in FIG. 4, the abscissa indicates an input pixel value, and the ordinate indicates an output pixel value.

Step S302:

Subsequently, the main memory 109 as micro coefficient memory means uses equation (15) to calculate a micro coefficient c(x) (coefficient for adding the high frequency component) of the gradation conversion curve F1( ), and stores the coefficient as a table c(x).

$$c(x) = 1 \Big/ \frac{\partial F1(x)}{\partial x} \qquad (15)$$

Here, "x" of the equation (15) is used as the variable indicating the pixel value. Moreover, "c(x)" has a function form in which for example, even when the dynamic range of the original image is changed, the amplitude of the high frequency component of the changed image matches with the amplitude of the high frequency component of the original image.

Figure 5:
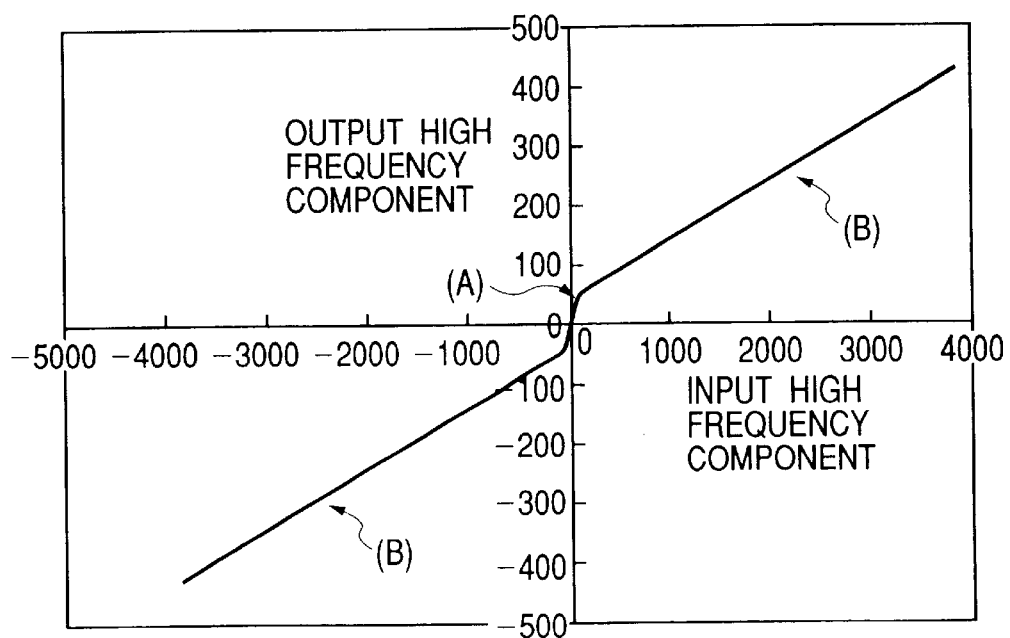
FIG. 5 is a diagram showing one example of a high frequency component conversion function for use in the conversion circuit of the dynamic range compression processing circuit.

Additionally, the conversion curve shown in FIG. 5 is a conversion curve (high frequency component conversion function Ch(x)) for use in the processing to change the high frequency component in the conversion circuit 204 described later, and in FIG. 5, the abscissa indicates the amplitude of the input high frequency component, and the ordinate indicates an output high frequency component obtained by converting the amplitude of the high frequency component. Moreover, the inclination of the conversion curve shown by (A) of FIG. 5 is set, for example, to "1", and the inclination of the conversion curve shown by (B) is set, for example, to "0.1". Here, the curve inclinations are experimentally determined in accordance with data properties.

Step S303:

Subsequently, the smoothing circuit 202 performs a smoothing processing shown by equation (16) to an image f0(x,y) after the gradation conversion processing of the gradation conversion circuit 201 to form a smoothed image fus(x,y) of the image f0(x,y).

$$fus(x, y) = \frac{\int_{-d}^{d}\int_{-d}^{d} f0(x+x1, y+y1)\,dx1\,dy1}{\int_{-d}^{d}\int_{-d}^{d} dx1\,dy1} \qquad (16)$$

In the equation (16), "d" indicates the mask size in the smoothing processing.

Additionally, the smoothing processing in the smoothing circuit 202 is not limited to the processing shown by the equation (16) and, for example, a smoothing processing using morphological filter calculation may be used as shown by equations (17) to (20).

$$f2(x,y)=\min\{f0(x+x1,y+y1)-D(x1,y1)|x1\times x1+y1\times y1 \leq r1\times r1\} \qquad (17)$$

$$f3(x,y)=\max\{f2(x+x1,y+y1)+D(x1,y1)|x1\times x1+y1\times y1 \leq r1\times r1\} \qquad (18)$$

$$f4(x,y)=\max\{f3(x+x1,y+y1)+D(x1,y1)|x1\times x1+y1\times y1 \leq r1\times r1\} \qquad (19)$$

$$fus(x,y)=\min\{f4(x+x1,y+y1)-D(x1,y1)|x1\times x1+y1\times y1 \leq r1\times r1\} \qquad (20)$$

In the equations (17) to (20), "D(x,y)" indicates a disc-shaped filter and is represented by equation (21) with an arbitrary constant r1 (constant to which a value is set in accordance with the original image, and the like).

$$D(x, y) = 0,\ x \times x + y \times y \leq r1 \times r1 \qquad (21)$$
$$= -\infty,\ \text{others}$$

Step S304:

Subsequently, the high frequency component generation circuit 203 calculates a high frequency component image fh(x,y) by equation (22) from the image f0(x,y) after the gradation conversion processing of the gradation conversion circuit 201 and the image fus(x,y) after the smoothing processing of the smoothing circuit 202.

$$fh(x,y)=c(f1(x,y))\times(f0(x,y)-fus(x,y)) \qquad (22)$$

In the equation (22) "c(x)" indicates the table c(x) stored beforehand in the main memory 109, that is, the coefficient of the gradation conversion curve F( ). Therefore, the high frequency component image fh(x,y) obtained here depends on the gradation conversion curve.

Step S305:

Subsequently, the conversion circuit 204 converts the high frequency component image fh(x,y) obtained in the high frequency component generation circuit 203 to calculate a converted image fch(x,y) by equation (23) which uses, for example, a high frequency component conversion function Ch(x) shown in FIG. 5.

$$fch(x,y)=Ch(fh(x,y)) \qquad (23)$$

Step S306:

Subsequently, the high frequency component addition circuit 205 adds the converted image fch(x,y) obtained in the conversion circuit 204 to the image fus(x,y) after the smoothing processing in the smoothing circuit 202. Specifically, an image fdr(x,y) after the final DRC processing is obtained by equation (24).

$$fdr(x,y)=f0(x,y)+(1-c(f1(x,y)))\times fch(x,y) \qquad (24)$$

Figure 6:
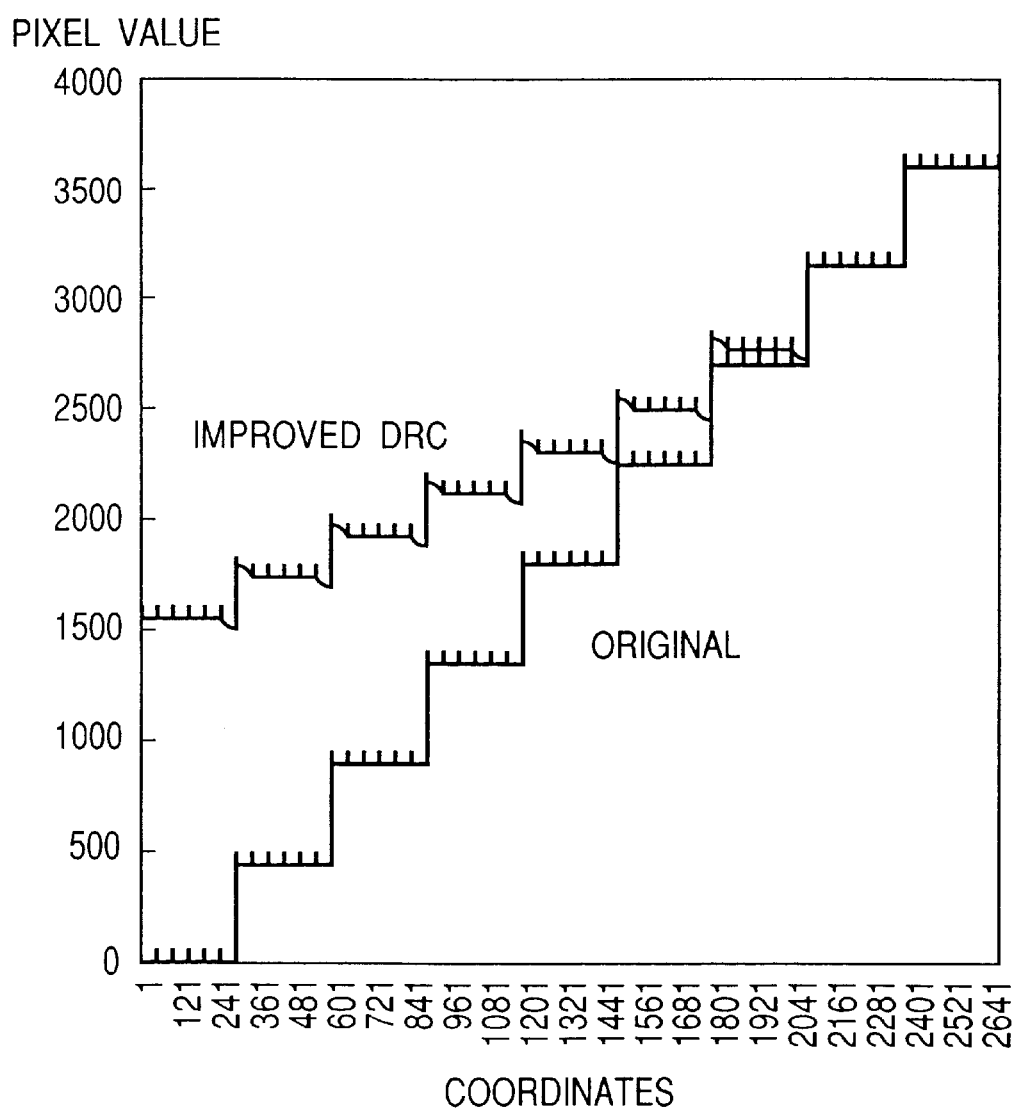
FIG. 6 is a diagram showing the state of a processed image obtained in the dynamic range compression processing circuit.
Figure 14:
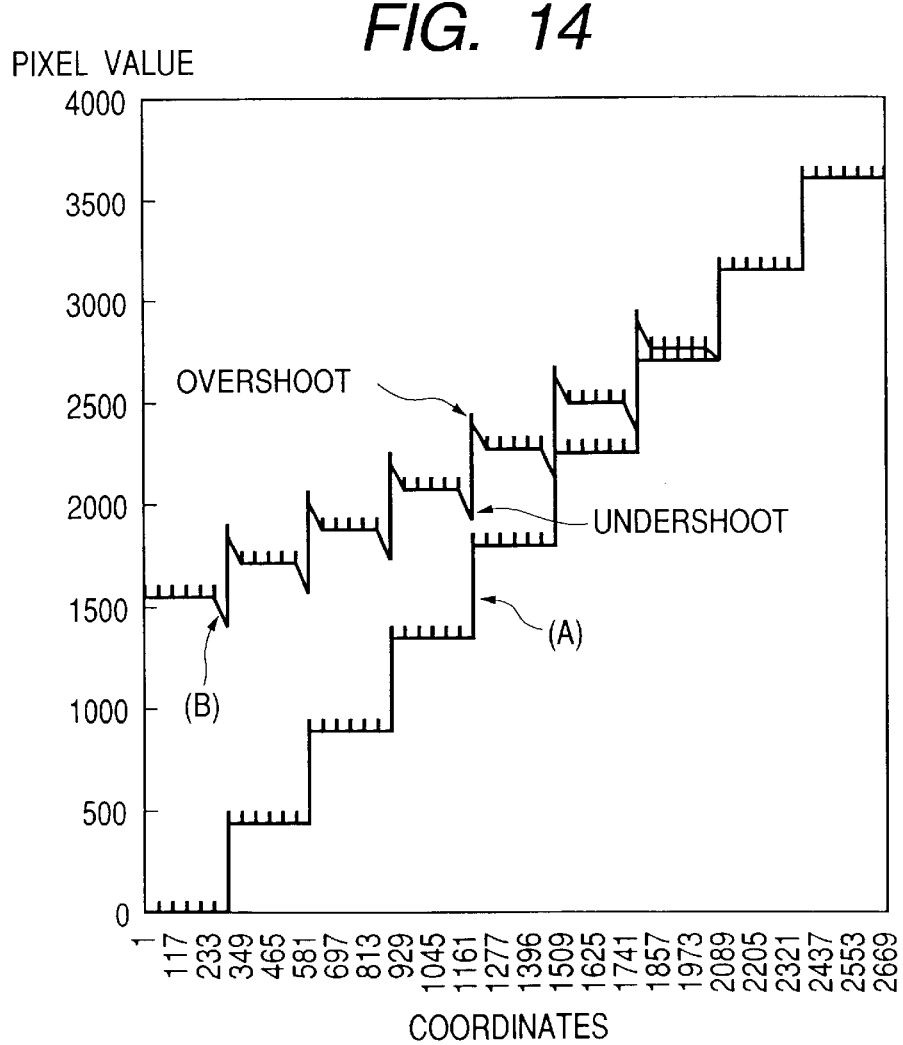
FIG. 14 is a diagram showing that an overshoot and undershoot are generated in the image by a conventional dynamic range compression processing.
Figure 15A:
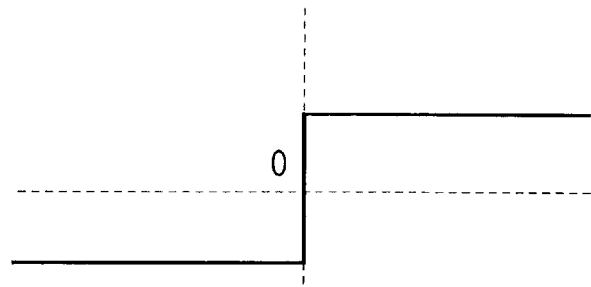
FIGS. 15A, 15B and 15C are explanatory views of the overshoot and undershoot.
Figure 15B:
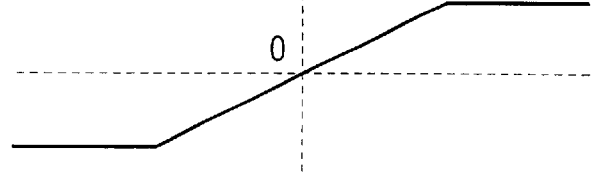
Figure 15C:
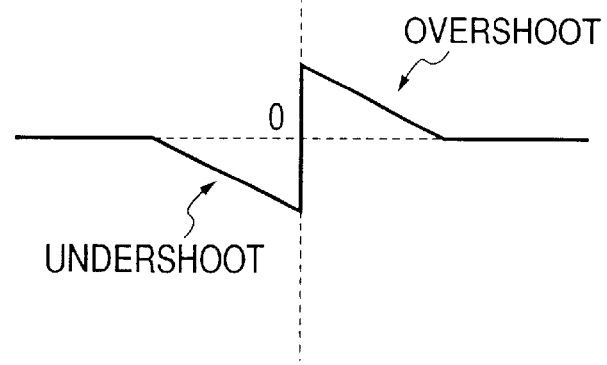

Here, FIG. 6 shows the profile of the image after the final DRC processing obtained in the high frequency component addition circuit 205. As apparent from FIG. 6, the change amount of the dynamic range is the same as that of the conventional DRC processing shown in FIG. 14, but the overshoot and undershoot are depressed.

Step S307:

As described above, the DRC processing circuit 112a obtains the image in which the artifacts such as the overshoot and undershoot are depressed, and supplies the image after the DRC processing to the gradation conversion circuit 112c.

In this case, the feature extraction circuit 112b extracts the feature amount for defining the gradation conversion curve for use in the gradation conversion circuit 112c from the image (original image) transferred via the CPU bus 107. Here, since the object image is a lung image, for example, the maximum pixel value in the lung area is extracted and used as the feature amount.

The gradation conversion circuit 112c defines the gradation conversion curve so that the feature amount (maximum pixel value) obtained in the feature extraction circuit 112b indicates a predetermined value (e.g., "1.8"), and uses the curve to perform the gradation conversion to the processed image of the DRC processing circuit 112a.

The processed image of the gradation conversion circuit 112c is displayed on the screen of the image display 111, or outputted onto the film.

As described above, in the present embodiment, for the high frequency component conversion function Ch(x) for use in converting the high frequency component, as shown in FIG. 5, as the absolute value of the high frequency component (input high frequency component) increases, the increase ratio of the absolute value of the converted high frequency component (output high frequency component) monotonously increases. By using such function, the amplitude of the high frequency component with a large amplitude is depressed with respect to the artifacts such as the overshoot and undershoot, and the amplitude of the frequency component with a small amplitude is unchanged with respect to the signal component of the object area. Since the high frequency component is converted in this manner, the artifacts can be depressed without dropping the signal component amplitude. Specifically, since the amplitude of the high frequency component regarded as the artifacts such as the overshoot and undershoot is larger than the amplitude of the high frequency component regarded as effective information, the artifacts can be depressed by the constitution for performing the conversion to depress the amplitude of the large-amplitude high frequency component.

Moreover, in the constitution, since the high frequency component dependent on the gradation conversion curve used in the gradation conversion processing (dependent on the coefficient c(x) of the gradation conversion curve F1( )) is added to the original image after the gradation conversion processing, the amplitude of the high frequency component of the image before the gradation conversion processing can be held even in the image after the gradation conversion processing.

Second Embodiment

Figure 7:
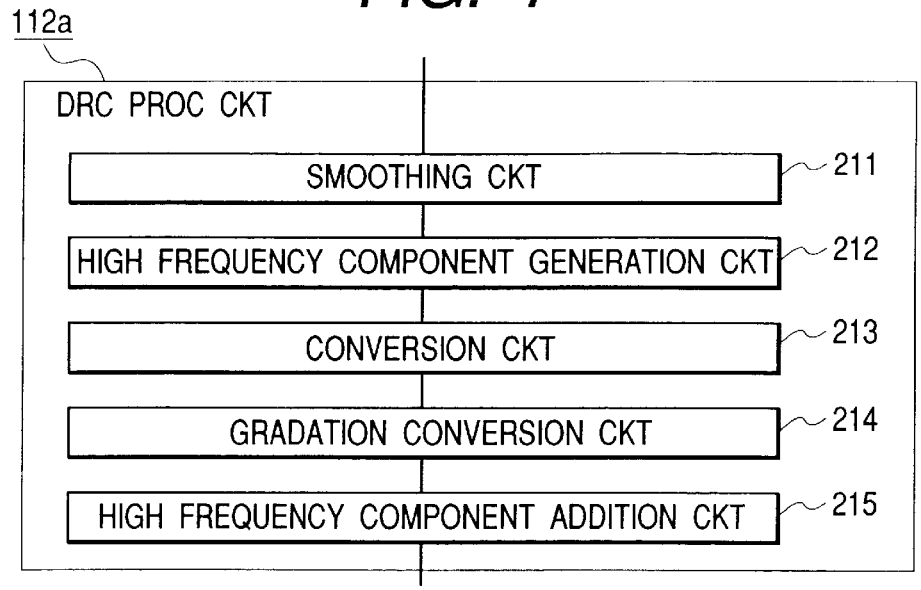
FIG. 7 is a block diagram showing the constitution of the dynamic range compression processing circuit of the X-ray photographing apparatus in a second embodiment.

In a second embodiment, in the X-ray photographing apparatus 100 of FIG. 1, the internal constitution of the DRC processing circuit 112a is constituted, for example, as shown in FIG. 7.

Specifically, the above-described first embodiment is constituted such that the high frequency component obtained from the image after the gradation conversion processing is converted, and added to the image after the gradation conversion processing, but the second embodiment is constituted such that the high frequency component obtained from the original image before the gradation conversion processing is converted and added to the original image after the gradation conversion processing.

Figure 8:
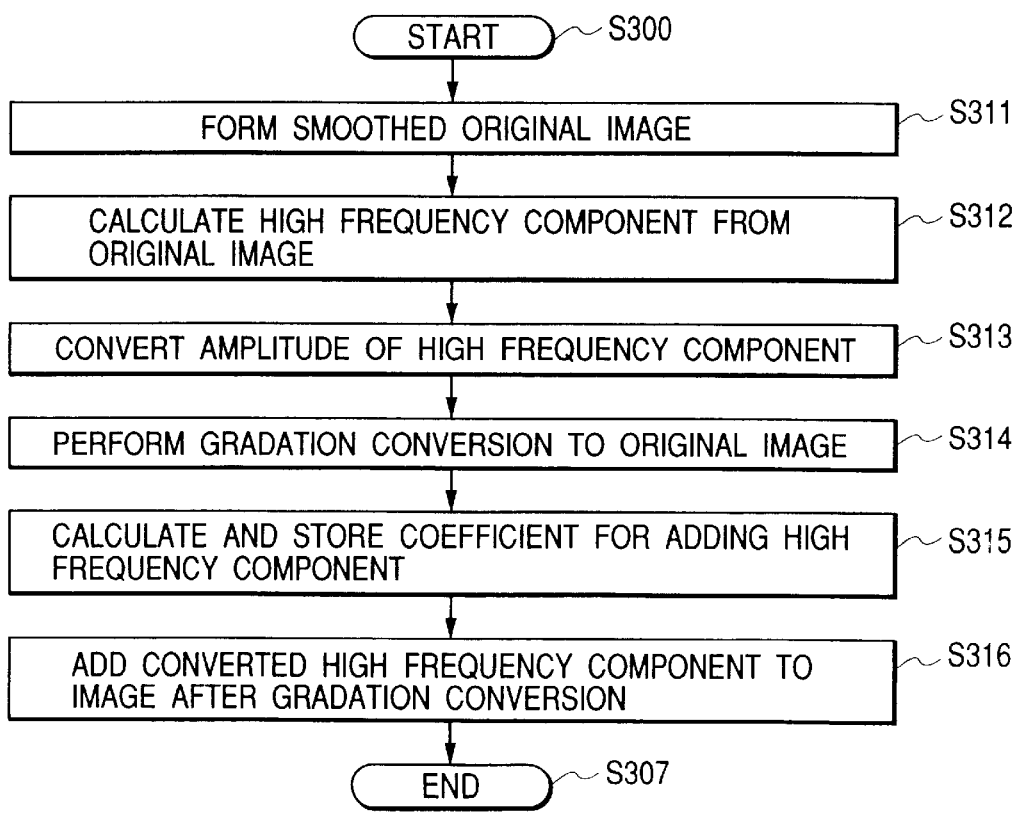
FIG. 8 is a flowchart showing the operation of the dynamic range compression processing circuit.

Therefore, for example, the processing program according to a flowchart of FIG. 8 is used as the processing program for the DRC processing here. Since the processing program is executed by the CPU 108, the X-ray photographing apparatus 100 operates as follows in the second embodiment.

Additionally, only the constitution different from that of the above-described first embodiment will concretely be described here.

Step S300:

First, similarly to the step S300 of FIG. 3, when the X-ray photographing operation starts, the X-ray image obtained by the photographing is transferred to the image processing circuit 112 via the data collection circuit 105 and preprocessing circuit 106 by the control of the CPU 108.

Subsequently, the DRC processing circuit 112a of the image processing circuit 112 executes the processing of the following steps S311 to S316.

Step S311:

First, a smoothing circuit 211 performs a smoothing processing shown by equation (25) to the X-ray image (original image) f1(x,y) transferred by the CPU 108 to form the smoothed image fus1(x,y) of the original image f1(x,y).

$$fus1(x, y) = \frac{\int_{-d}^{d}\int_{-d}^{d} f1(x+x1, y+y1) dx1 dy1}{\int_{-d}^{d}\int_{-d}^{d} dx1 dy1} \qquad (25)$$

In the equation (25), "d" indicates a constant for determining the mask size M×M in the smoothing processing.

Step S312:

Subsequently, a high frequency component generation circuit 212 calculates a high frequency component image fh1(x,y) by equation (26) from the original image f1(x,y) transferred by the CPU 108 and the image fus1(x,y) after the smoothing processing of the smoothing circuit 211.

$$fh1(x,y)=f1(x,y)-fus1(x,y) \qquad (26)$$

Step S313:

Subsequently, a conversion circuit 213 converts the high frequency component image fh1(x,y) obtained by the high frequency component generation circuit 212, and calculates a converted image fch1(x,y) by equation (27) which uses the high frequency component conversion function Ch(x) shown in FIG. 5.

$$fch1(x,y)=Ch(fh1(x,y)) \qquad (27)$$

Step S314:

Subsequently, a gradation conversion circuit 214 performs a gradation conversion processing shown by equation

(28) to the original image transferred by the CPU 108, using the gradation conversion curve F1( ) shown in FIG. 4.

$$f0(x,y)=F1(f1(x,y)) \tag{28}$$

In the equation (28), "f1(x,y)" indicates the pixel value of the original image (two-dimensional original image) as the processing object, and "x" and "y" indicate two-dimensional X and Y coordinates of the original image. Moreover, "f0(x,y)" indicates the pixel value of the original image (output image) after the gradation conversion processing.

Step S315:

Subsequently, the main memory 109 as the micro coefficient memory means uses equation (29) to calculate a micro coefficient c1(x) of the gradation conversion curve F1( ), and stores the coefficient as a table c1(x).

$$c1(x) = 1 - \frac{\partial F1(x)}{\partial x} \tag{29}$$

Step S316:

Subsequently, a high frequency component addition circuit 215 adds a converted image fc1h(x,y) of the conversion circuit 213 to the image f0(x,y) after the gradation conversion processing of the gradation conversion circuit 214. Specifically, an image fdr1(x,y) after the final DRC processing is calculated by equation (30).

$$fdr1(x,y)=f0(x,y)+c(f1(x,y))\times fch1(x,y) \tag{30}$$

Step S307:

As described above, the image fdr1(x,y) after the DRC processing obtained by the DRC processing circuit 112a is supplied to the gradation conversion circuit 112c similarly to the step S307 of FIG. 3, subjected to the gradation conversion processing, and subsequently displayed on the screen of the image display 111 or outputted onto the film.

As described above, in the present embodiment, since the high frequency component of the original image before the gradation conversion processing is used to perform the DRC processing, as compared with the DRC processing using the high frequency component of the original image after the gradation conversion processing, the DRC processing can be performed using a more precise (less digit drop) high frequency component. In addition to the effect of the first embodiment, this can provide an effect that a higher frequent component image with a satisfactory restorability can be obtained after the DRC processing.

Third Embodiment

Figure 9:
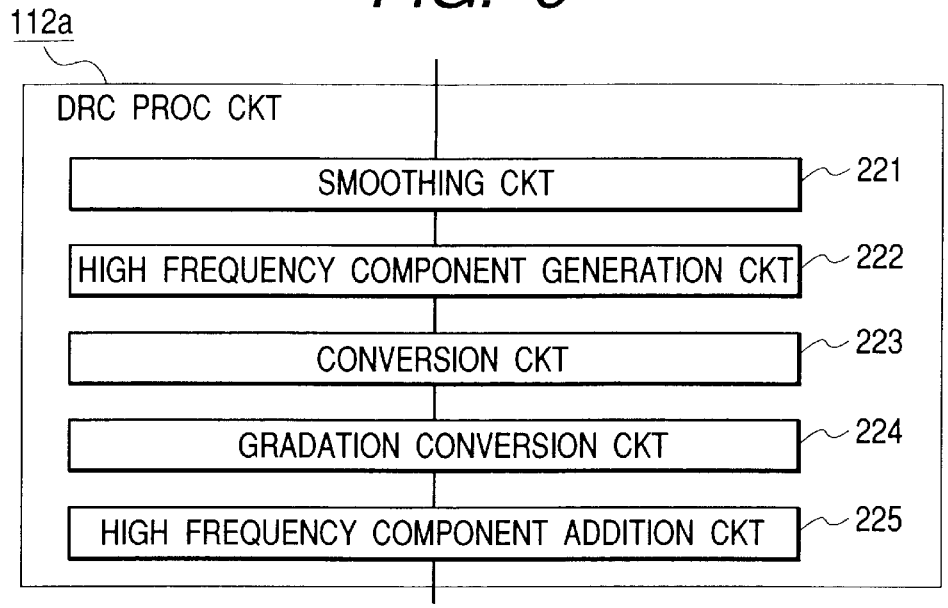
FIG. 9 is a block diagram showing the constitution of the dynamic range compression processing circuit of the X-ray photographing apparatus in a third embodiment.

According to a third embodiment, in the X-ray photographing apparatus 100 of FIG. 1, the internal constitution of the DRC processing circuit 112a is constituted, for example, as shown in FIG. 9.

Specifically, the above-described first embodiment is constituted such that the high frequency component obtained from the image after the gradation conversion processing is converted and added to the image after the gradation conversion processing, but the third embodiment is constituted such that the high frequency component obtained from the original image before the gradation conversion processing is converted and added to the original image after the smoothing processing and gradation conversion processing.

Figure 10:
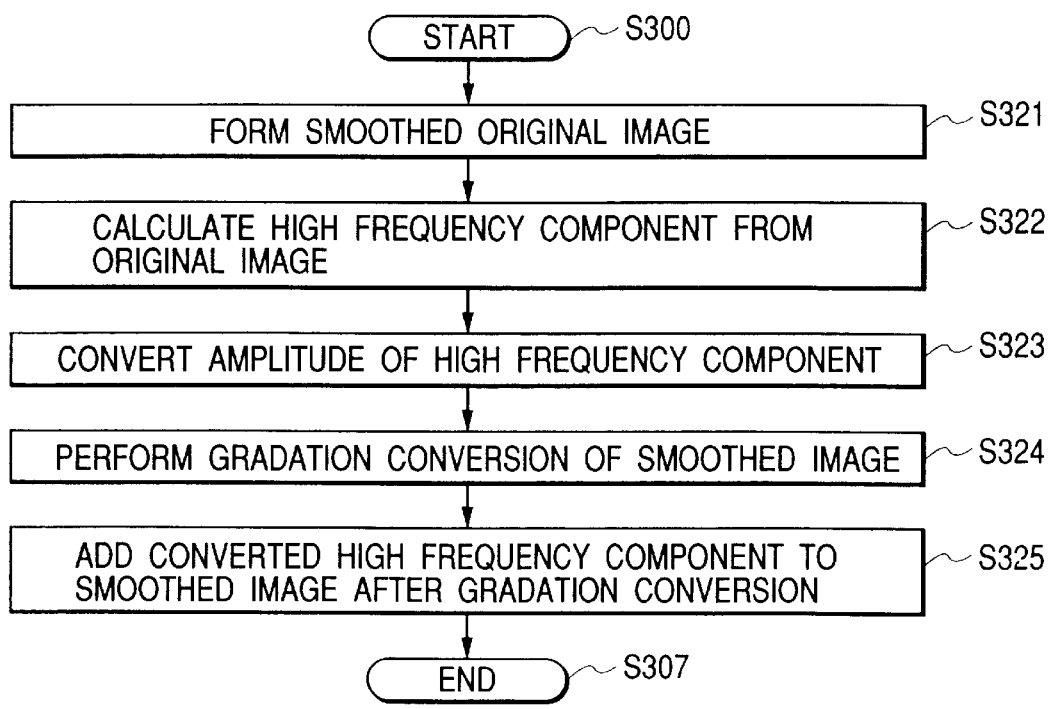
FIG. 10 is a flowchart showing the operation of the dynamic range compression processing circuit.

Therefore, for example, the processing program according to a flowchart of FIG. 10 is used as the processing program for the DRC processing here. Since the processing program is executed by the CPU 108, the X-ray photographing apparatus 100 operates as follows in the third embodiment.

Additionally, only the constitution different from that of the above-described first embodiment will concretely be described here.

Step S300:

First, similarly to the step S300 of FIG. 3, when the X-ray photographing operation starts, the X-ray image obtained by the photographing is transferred to the image processing circuit 112 via the data collection circuit 105 and preprocessing circuit 106 by the control of the CPU 108.

Subsequently, the DRC processing circuit 112a of the image processing circuit 112 executes the processing of the following steps S321 to S325.

Step S321:

First, a smoothing circuit 221 performs a smoothing processing shown by equation (31) to the X-ray image (original image) f1(x,y) transferred by the CPU 108 to form the smoothed image fus1(x,y) of the original image f1(x,y).

$$fus1(x,y) = \frac{\int_{-d}^{d}\int_{-d}^{d} f1(x+x1, y+y1)dx1\,dy1}{\int_{-d}^{d}\int_{-d}^{d} dx1\,dy1} \tag{31}$$

In the equation (31), "d" indicates the constant for determining the mask size M×M in the smoothing processing.

Step S322:

Subsequently, a high frequency component generation circuit 222 calculates a high frequency component image fh1(x,y) by equation (32) from the original image f1(x,y) transferred by the CPU 108 and the image fus1(x,y) after the smoothing processing in the smoothing circuit 221.

$$fh1(x,y)=f1(x,y)-fus1(x,y) \tag{32}$$

Step S323:

Subsequently, a conversion circuit 223 converts the high frequency component image fh1(x,y) obtained in the high frequency component generation circuit 222, and calculates a converted image fch1(x,y) by equation (33) which uses the high frequency component conversion function Ch(x) shown in FIG. 5.

$$fch1(x,y)=Ch(fh1(x,y)) \tag{33}$$

Step S324:

Subsequently, a gradation conversion circuit 224 performs a gradation conversion processing shown by equation (34) to the image fus1(x,y) after the smoothing processing of the smoothing circuit 221, using the gradation conversion curve F1( ) shown in FIG. 4.

$$fus2(x,y)=F1(fus1(x,y)) \tag{34}$$

In the equation (34), "fus2(x,y)" indicates the pixel value of the smoothed image (output image) after the gradation conversion processing.

Step S325:

Subsequently, a high frequency component addition circuit 225 adds the converted image fc1h(x,y) of the conversion circuit 223 to the image fus2(x,y) (image after the smoothing processing and gradation conversion processing) after the gradation conversion processing of the gradation conversion circuit 224. Specifically, an image fdr2(x,y) after the final DRC processing is calculated by equation (35).

$$fdr2(x,y)=fus2(x,y)+fch1(x,y) \tag{35}$$

Step S307:

As described above, the image fdr2(x,y) after the DRC processing obtained by the DRC processing circuit 112a is supplied to the gradation conversion circuit 112c similarly to the step S307 of FIG. 3, subjected to the gradation conversion processing, and subsequently displayed on the screen of the image display 111 or outputted onto the film.

As described above, in the third embodiment, since the high frequency component of the original image before the gradation conversion processing is used, and the converted component is added to the image after the smoothing processing and gradation conversion processing, as compared with the DRC processing in which the high frequency component of the original image after the gradation conversion is used, the DRC processing can be performed using a more precise (less digit drop) high frequency component. In addition to the effect of the first embodiment, this can provide an effect that a higher frequent component image with a satisfactory restorability can be obtained after the DRC processing. Furthermore, since the gradation conversion is performed after obtaining and converting the high frequency component, in the above-described first (or second) embodiment, the processing of calculating and storing the coefficient c(x) of the gradation conversion curve F( ) is unnecessary. In the gradation conversion of the original image, the high frequency component needs to be considered in the gradation conversion, but in the third embodiment, the smoothed image (image with no high frequency component) is subjected to the gradation conversion, and the high frequency component does not have to be considered in the gradation conversion. Therefore, the processing time can be shortened.

Fourth Embodiment

Figure 11:
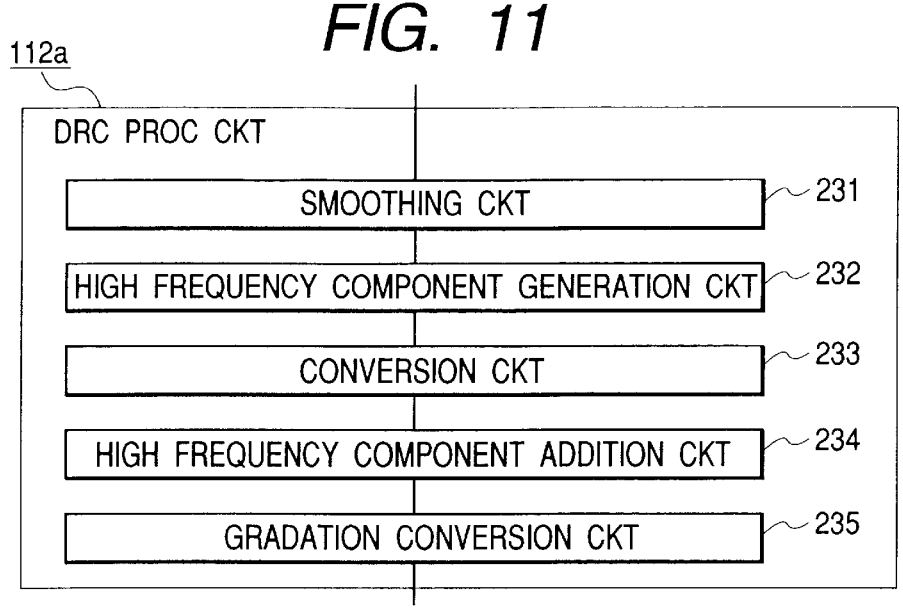
FIG. 11 is a block diagram showing the constitution of the dynamic range compression processing circuit of the X-ray photographing apparatus in a fourth embodiment.

According to a fourth embodiment, in the X-ray photographing apparatus 100 of FIG. 1, the internal constitution of the DRC processing circuit 112a is constituted, for example, as shown in FIG. 11.

Specifically, the above-described first embodiment is constituted such that the high frequency component obtained from the image after the gradation conversion processing is converted and added to the image after the gradation conversion processing, but the fourth embodiment is constituted such that the high frequency component obtained from the original image before the gradation conversion processing is converted, added to the original image, and subsequently subjected to the gradation conversion processing.

Figure 12:
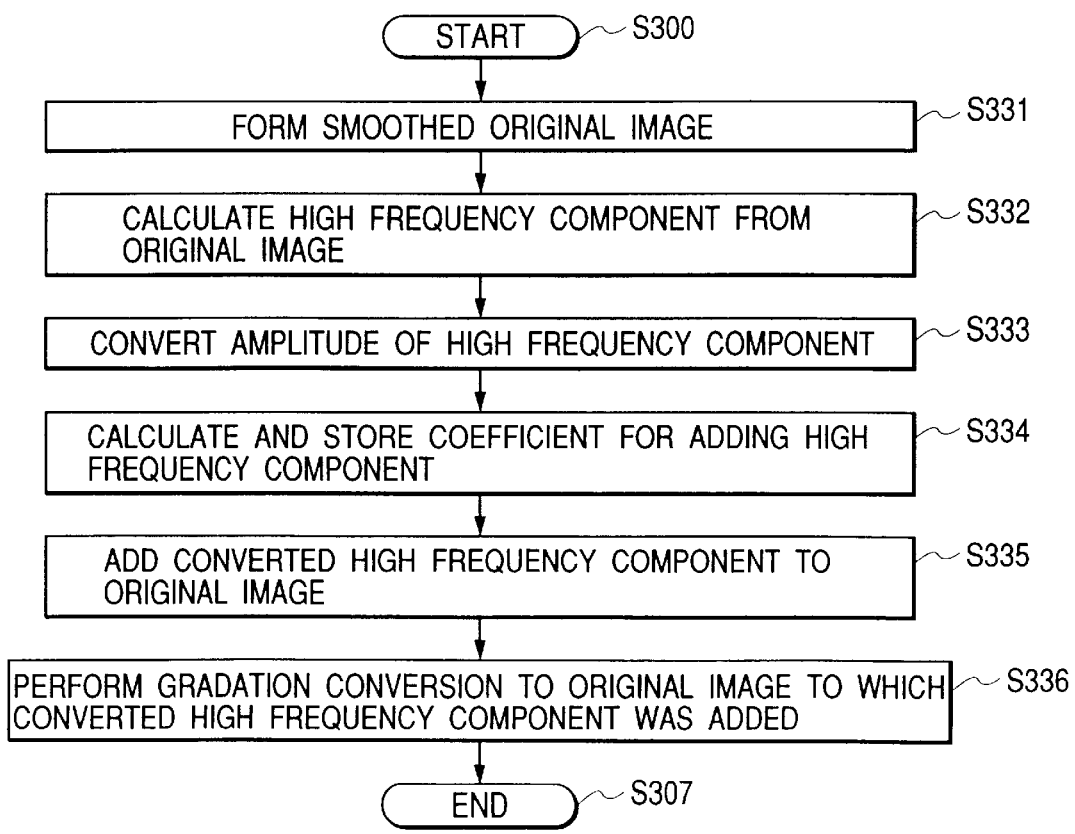
FIG. 12 is a flowchart showing the operation of the dynamic range compression processing circuit.

Therefore, for example, the processing program according to a flowchart of FIG. 12 is used as the processing program for the DRC processing here. Since the processing program is executed by the CPU 108, the X-ray photographing apparatus 100 operates as follows in the fourth embodiment.

Additionally, only the constitution different from that of the above-described first embodiment will concretely be described here.

Step S300:

First, similarly to the step S300 of FIG. 3, when the X-ray photographing operation starts, the X-ray image obtained by the photographing is transferred to the image processing circuit 112 via the data collection circuit 105 and preprocessing circuit 106 by the control of the CPU 108.

Subsequently, the DRC processing circuit 112a of the image processing circuit 112 executes the processing of the following steps S331 to S335.

Step S331:

First, a smoothing circuit 231 performs a smoothing processing shown by equation (36) to the X-ray image (original image) f1(x,y) transferred by the CPU 108 to form the smoothed image fus1(x,y) of the original image f1(x,y).

$$fus1(x, y) = \frac{\int_{-d}^{d}\int_{-d}^{d} f1(x+x1, y+y1) dx1 dy1}{\int_{-d}^{d}\int_{-d}^{d} dx1 dy1} \quad (36)$$

In the equation (36), "d" indicates the constant for determining the mask size M×M in the smoothing processing.

Step S332:

Subsequently, a high frequency component generation circuit 232 calculates a high frequency component image fh1(x,y) by equation (37) from the original image f1(x,y) transferred by the CPU 108 and the image fus1(x,y) after the smoothing processing of the smoothing circuit 231.

$$fh1(x,y)=f1(x,y)-fus1(x,y) \quad (37)$$

Step S333:

Subsequently, a conversion circuit 233 converts the high frequency component image fh1(x,y) obtained by the high frequency component generation circuit 232, and calculates a converted image fch1(x,y) by equation (38) which uses the high frequency component conversion function Ch(x) shown in FIG. 5.

$$fch1(x,y)=Ch(fh1(x,y)) \quad (38)$$

Step S334:

Subsequently, the main memory 109 as the micro coefficient memory means uses equation (39) to calculate the micro coefficient c1(x) of the gradation conversion curve F1( ) for use in a gradation conversion circuit 235, and stores the coefficient as a table c2(x).

$$c2(x) = 1 / \frac{\partial F1(x)}{\partial x} - 1 \quad (39)$$

Step S335:

A high frequency component addition circuit 234 adds the converted image fc1h(x,y) of the conversion circuit 233 to the original image f1(x,y). Specifically, an image fad(x,y) after the addition of the high frequency component is calculated by equation (40).

$$fad(x,y)=f1(x,y)+c2(f1(x,y))\times fch1(x,y) \quad (40)$$

Step S336:

Subsequently, the gradation conversion circuit 235 uses the gradation conversion curve F1( ) shown in FIG. 4 and performs a gradation conversion processing shown by equation (41) to the image fad(x,y) obtained by the high frequency component addition circuit 234 to obtain the image fdr2(x,y) after the final DRC processing.

$$fdr2(x,y)=F1(fad(x,y)) \quad (41)$$

Step S307:

The above-described image fdr2(x,y) after the DRC processing obtained by the DRC processing circuit 112a is supplied to the gradation conversion circuit 112c similarly to the step S307 of FIG. 3, subjected to the gradation conversion processing, and subsequently displayed on the screen of the image display 111 or outputted onto the film.

As described above, in the fourth embodiment, since the high frequency component of the original image before the gradation conversion processing is used to perform the DRC processing, as compared with the DRC processing in which the high frequency component of the original image after the gradation conversion processing is used, the DRC processing can be performed using a more precise (less digit drop) high frequency component. In addition to the effect of the first embodiment, this can provide an effect that a higher frequent component image with a satisfactory restorability can be obtained after the DRC processing.

Fifth Embodiment

In the above-described first to fourth embodiments, by using the high frequency component conversion function shown in FIG. 5 to convert the magnitude of the amplitude of the high frequency component obtained from the original image or the image obtained by smoothing the original image in accordance with the magnitude of the high frequency component, the artifacts such as the overshoot and undershoot are depressed.

Figure 13:
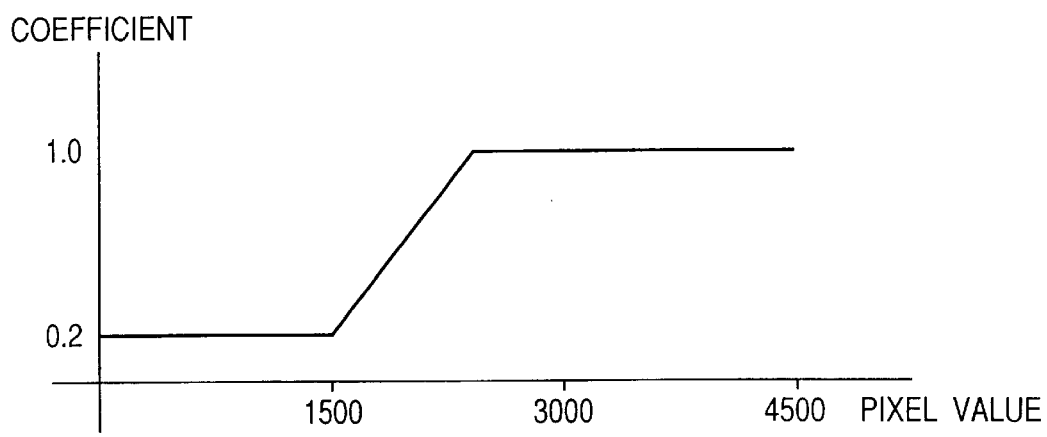
FIG. 13 is a diagram showing one example of the high frequency component conversion function for use in the conversion circuit of the dynamic range compression processing circuit in a fifth embodiment.

On the other hand, in a fifth embodiment, for example, by using a high frequency component conversion function as shown in FIG. 13 to convert the magnitude of the amplitude of the high frequency component obtained from the original image or the smoothed image of the original image in accordance with the magnitude of the pixel value, the emphasis of the noise is depressed. The fifth embodiment will concretely be described hereinafter.

Additionally, here, the embodiments for using the high frequency component conversion function of FIG. 13 to convert the high frequency component in the conversion processing 204, 213, 223, 233 of the above-described first to fourth embodiments will be described hereinafter as first' to fourth' embodiments. Moreover, since the constitution of the DRC processing circuit 112a in the fifth embodiment is similar to the internal constitution of the DRC processing circuit 112a in the first to fourth embodiments shown in FIGS. 2, 3, and 7 to 12, these drawings will be used in the following description.

(1) First' Embodiment: See FIGS. 2 and 3
Step S300:
 First, as described above, when the X-ray photographing operation starts, the X-ray image obtained by the photographing is transferred to the image processing circuit 112 via the data collection circuit 105 and preprocessing circuit 106 by the control of the CPU 108.
 Subsequently, the DRC processing circuit 112a of the image processing circuit 112 executes the processing of the following steps S301 to S306.
Step S301:
 First, the gradation conversion circuit 201 uses the gradation conversion curve F1( ) defined by the feature amount extracted by the feature extraction circuit 112b and shown in FIG. 4 to perform the gradation conversion processing shown in the equation (14) to the image (original image) transferred via the CPU bus 107.

$$f0(x,y)=F1(f1(x,y)) \quad (14)$$

In the equation (14), "f1(x,y)" indicates the pixel value of the original image (two-dimensional original image) which is a processing object, and "x" and "y" indicate two-dimensional X and Y coordinates of the original image. Moreover, "f0(x,y)" indicates the pixel value of the original image (output image) after the gradation conversion processing.
Step S302:
 Subsequently, the main memory 109 as the micro coefficient memory means uses the equation (15) to calculate the micro coefficient c(x) (coefficient for adding the high frequency component) of the gradation conversion curve F1( ), and stores the coefficient as the table c(x).

$$c(x) = 1 / \frac{\partial F1(x)}{\partial x} \quad (15)$$

Here, "x" of the equation (15) is used as the variable indicating the pixel value. Moreover, "c(x)" has a function form in which for example, even when the dynamic range of the original image is changed, the amplitude of the high frequency component of the changed image matches with the amplitude of the high frequency component of the original image. Additionally, in the processing of changing the high frequency component as described later, this applies to a case in which the high frequency component conversion function of FIG. 13 is used as the conversion curve for use in the processing and the high frequency component is not changed.

Additionally, the high frequency component conversion function in the present embodiment shown in FIG. 13 is one example of the conversion curve for use in the processing to change the high frequency component in the conversion circuit 204, and in FIG. 13, the abscissa indicates the pixel value, and the ordinate indicates a coefficient to be multiplied by the high frequency component.
Step S303:
 Subsequently, the smoothing circuit 202 performs the smoothing processing shown by the equation (16) to the image f0(x,y) after the gradation conversion processing in the gradation conversion circuit 201 to form the smoothed image fus(x,y) of the image f0(x,y).

$$fus(x, y) = \frac{\int_{-d}^{d}\int_{-d}^{d} f0(x+x1, y+y1) dx1 dy1}{\int_{-d}^{d}\int_{-d}^{d} dx1 dy1} \quad (16)$$

In the equation (16), "d" indicates the constant for determining the mask size M×M in the smoothing processing.
 Additionally, the smoothing processing in the smoothing circuit 202 is not limited to the processing shown by the equation (16) and, for example, the smoothing processing which uses the morphological filter calculation may be used as shown by equations (17) to (20).
calculation may be used as shown by equations (17) to (20).

$$f2(x,y)=\min\{f0(x+x1,y+y1)-D(x1,y1)|x1 \times x1+y1 \times y1 \leq r1 \times r1\} \quad (17)$$

$$f3(x,y)=\max\{f2(x+x1,y+y1)+D(x1,y1)|x1 \times x1+y1 \times y1 \leq r1 \times r1\} \quad (18)$$

$$f4(x,y)=\max\{f3(x+x1,y+y1)+D(x1,y1)|x1 \times x1+y1 \times y1 \leq r1 \times r1\} \quad (19)$$

$$fus(x,y)=\min\{f4(x+x1,y+y1)-D(x1,y1)|x1 \times x1+y1 \times y1 \leq r1 \times r1\} \quad (20)$$

In the equations (17) to (20), "D(x,y)" indicates the disc-shaped filter and is represented by the equation (21) with the arbitrary constant r1 (constant to which the value is set in accordance with the original image, and the like).

$$D(x, y) = 0, \ x \times x + y \times y \leq r1 \times r1 \quad (21)$$
$$= -\infty, \text{ others}$$

By using the morphological filter calculation to perform the smoothing processing, the structure of the original image can be held even in the edge part of the original image, so that the artifacts such as the overshoot and undershoot can be depressed.

Step S304:

Subsequently, the high frequency component generation circuit 203 calculates the high frequency component image fh(x,y) by the equation (22) from the image f0(x,y) after the gradation conversion processing of the gradation conversion circuit 201 and the image fus(x,y) after the smoothing processing in the smoothing circuit 202.

$$fh(x,y)=c(f1(x,y))\times(f0(x,y)-fus(x,y)) \qquad (22)$$

Step S305:

Subsequently, the conversion circuit 204 converts the high frequency component image fh(x,y) obtained in the high frequency component generation circuit 203 to calculate the converted image fch(x,y) by equation (23') based on the high frequency component conversion function Ch(x) of FIG. 13.

$$fch(x,y)=Ch(f1(x,y))\times fh(x,y) \qquad (23')$$

Additionally, the high frequency component conversion function Ch(x) of FIG. 13 may have any function system as long as the coefficient of the area in which the high frequency component amplitude is to be depressed is subtracted. Moreover, the original image f1(x,y) is used as the image in the coefficient "Ch( )" here, but this is not limited, and for example, the image obtained after smoothing the original image, the image after the gradation conversion of the original image, or the image smoothed after the gradation conversion of the original image may be used.

Step S306:

Subsequently, the high frequency component addition circuit 205 adds the converted image fch(x,y) obtained in the conversion circuit 204 to the image fus(x,y) after the smoothing processing in the smoothing circuit 202. Specifically, the image fdr(x,y) after the final DRC processing is calculated by equation (24').

$$fdr(x,y)=f0(x,y)+(1-1/c(f1(x,y)))\times fch(x,y) \qquad (24')$$

Step S307:

Thereafter, as described above, the image fdr1(x,y) after the DRC processing obtained by the DRC processing circuit 112a is supplied to the gradation conversion circuit 112c, subjected to the gradation conversion processing, and displayed on the screen of the image display 111 or outputted onto the film.

As described above, in the constitution of the present embodiment, since the high frequency component dependent on the gradation conversion curve used in the gradation conversion processing (dependent on the coefficient c(x) of the gradation conversion curve F1( )) is added to the original image after the gradation conversion processing, the amplitude of the high frequency component of the image before the gradation conversion processing can be held even in the image after the gradation conversion processing. Moreover, since the high frequency component of the noise area is not restored, the image area of the low frequency component of the noise area can easily be observed. Furthermore, by using the morphological filter calculation in the smoothing processing, the structure of the original image can be held even in the edge part of the original image, so that the artifacts such as the overshoot and undershoot can be depressed.

(2) Second' Embodiment: see FIGS. 7 and 8

Step S300:

First, as described above, when the X-ray photographing operation starts, the X-ray image obtained by the photographing is transferred to the image processing circuit 112 via the data collection circuit 105 and preprocessing circuit 106 by the control of the CPU 108.

Subsequently, the DRC processing circuit 112a of the image processing circuit 112 executes the processing of the following steps S311 to S316.

Step S311:

First, the smoothing circuit 211 performs the smoothing processing shown by the equation (25) to the X-ray image (original image) f1(x,y) transferred by the CPU 108 to form the smoothed image fus1(x,y) of the original image f1(x,y).

$$fus1(x,y) = \frac{\int_{-d}^{d}\int_{-d}^{d} f1(x+x1, y+y1)\,dx1\,dy1}{\int_{-d}^{d}\int_{-d}^{d} dx1\,dy1} \qquad (25)$$

In the equation (25), "d" indicates the constant for determining the mask size M×M in the smoothing processing.

Step S312:

Subsequently, the high frequency component generation circuit 212 calculates the high frequency component image fh1(x,y) by the equation (26) from the original image f1(x,y) transferred by the CPU 108 and the image fus1(x,y) after the smoothing processing of the smoothing circuit 211.

$$fh1(x,y)=f1(x,y)-fus1(x,y) \qquad (26)$$

Step S313:

Subsequently, the conversion circuit 213 converts the high frequency component image fh1(x,y) obtained in the high frequency component generation circuit 212, and calculates the converted image fch1(x,y) by equation (27') based on the high frequency component conversion function Ch(x) of FIG. 13.

$$fch1(x,y)=Ch(f1(x,y))\times fh1(x,y) \qquad (27')$$

Step S314:

Subsequently, the gradation conversion circuit 214 performs the gradation conversion processing shown by the equation (28) to the original image transferred by the CPU 108, using the gradation conversion curve F1( ) shown in FIG. 4.

$$f0(x,y)=F1(f1(x,y)) \qquad (28)$$

In the equation (28), "f1(x,y)" indicates the pixel value of the original image (two-dimensional original image) as the processing object, and "x" and "y" indicate two-dimensional X and Y coordinates of the original image. Moreover, "f0(x,y)" indicates the pixel value of the original image (output image) after the gradation conversion processing.

Step S315:

Subsequently, the main memory 109 as the micro coefficient memory means uses the equation (29) to calculate the micro coefficient c1(x) of the gradation conversion curve F1( ), and stores the coefficient as the table c1(x).

$$c1(x) = 1 - \frac{\partial F1(x)}{\partial x} \qquad (29)$$

Step S316:

Subsequently, the high frequency component addition circuit 215 adds the converted image fc1h(x,y) in the conversion circuit 213 to the image f0(x,y) after the gradation conversion processing in the gradation conversion circuit 214. Specifically, the image fdr1(x,y) after the final DRC processing is calculated by the equation (30).

$$fdr1(x,y)=f0(x,y)+c(f1(x,y))\times fch1(x,y) \quad (30)$$

Step S307:

Thereafter, as described above, the image fdr1(x,y) after the DRC processing obtained by the DRC processing circuit 112a is supplied to the gradation conversion circuit 112c, subjected to the gradation conversion processing, and subsequently displayed on the screen of the image display 111 or outputted onto the film.

As described above, in the present embodiment, since the high frequency component of the original image before the gradation conversion processing is used to perform the DRC processing, as compared with the DRC processing which uses the high frequency component of the original image after the gradation conversion processing, the DRC processing can be performed using a more precise (less digit drop) high frequency component. In addition to the effect of the first' embodiment, this can provide an effect that a higher frequent component image with a satisfactory restorability can be obtained after the DRC processing.

(3) Third' Embodiment: see FIGS. 9 and 10

Step S300:

First, as described above, when the X-ray photographing operation starts, the X-ray image obtained by the photographing is transferred to the image processing circuit 112 via the data collection circuit 105 and preprocessing circuit 106 by the control of the CPU 108.

Subsequently, the DRC processing circuit 112a of the image processing circuit 112 executes the processing of the following steps S321 to S325.

Step S321:

First, the smoothing circuit 221 performs the smoothing processing shown by the equation (31) to the X-ray image (original image) f1(x,y) transferred by the CPU 108 to form the smoothed image fus1(x,y) of the original image f1(x,y).

$$fus1(x, y) = \frac{\int_{-d}^{d}\int_{-d}^{d} f1(x+x1, y+y1) dx1 dy1}{\int_{-d}^{d}\int_{-d}^{d} dx1 dy1} \quad (31)$$

In the equation (31), "d" indicates the constant for determining the mask size M×M in the smoothing processing.

Step S322:

Subsequently, the high frequency component generation circuit 222 calculates the high frequency component image fh1(x,y) by the equation (32) from the original image f1(x,y) transferred by the CPU 108 and the image fus1(x,y) after the smoothing processing in the smoothing circuit 221.

$$fh1(x,y)=f1(x,y)-fus1(x,y) \quad (32)$$

Step S323:

Subsequently, the conversion circuit 223 converts the high frequency component image fh1(x,y) obtained by the high frequency component generation circuit 222, and calculates the converted image fch1(x,y) by equation (33') based on the high frequency component conversion function Ch(x) of FIG. 13.

$$fch1(x,y)=Ch(f1(x,y))\times fh1(x,y) \quad (33')$$

Step S324:

Subsequently, the gradation conversion circuit 224 performs the gradation conversion processing shown by the equation (34) to the image fus1(x,y) after the smoothing processing in the smoothing circuit 221, using the gradation conversion curve F1( ) shown in FIG. 4.

$$fus2(x,y)=F1(fus1(x,y)) \quad (34)$$

In the equation (34), "fus2(x,y)" indicates the pixel value of the smoothed image (output image) after the gradation conversion processing.

Step S325:

Subsequently, the high frequency component addition circuit 225 adds the converted image fc1h(x,y) in the conversion circuit 223 to the image fus2(x,y) (image after the smoothing processing and gradation conversion processing) after the gradation conversion processing in the gradation conversion circuit 224. Specifically, then image fdr2(x,y) after the final DRC processing is calculated by the equation (35).

$$fdr2(x,y)=fus2(x,y)+fch1(x,y) \quad (35)$$

Step S307:

Thereafter, as described above, the image fdr2(x,y) after the DRC processing obtained by the DRC processing circuit 112a is supplied to the gradation conversion circuit 112c, subjected to the gradation conversion processing, and subsequently displayed on the screen of the image display 111 or outputted onto the film.

As described above, in the present embodiment, since the high frequency component of the original image before the gradation conversion processing is used, and the converted component is added to the image after the smoothing processing and gradation conversion processing, as compared with the DRC processing which uses the high frequency component of the original image after the gradation conversion, the DRC processing can be performed using a more precise (less digit drop) high frequency component. In addition to the effect of the first' embodiment, this can provide an effect that a higher frequent component image with a satisfactory restorability can be obtained after the DRC processing. Furthermore, since the gradation conversion is performed after obtaining and converting the high frequency component, in the above-described first' (or second') embodiment, the processing of calculating and storing the coefficient c(x) of the gradation conversion curve F( ) is unnecessary, and the processing time can be shortened.

(4) Fourth' Embodiment: see FIGS. 11 and 12

Step S300:

First, as described above, when the X-ray photographing operation starts, the X-ray image obtained by the photographing is transferred to the image processing circuit 112 via the data collection circuit 105 and preprocessing circuit 106 by the control of the CPU 108.

Subsequently, the DRC processing circuit 112a of the image processing circuit 112 executes the processing of the following steps S331 to S335.

Step S331:

First, the smoothing circuit 231 performs the smoothing processing shown by the equation (36) to the X-ray image (original image) f1(x,y) transferred by the CPU 108 to form the smoothed image fus1(x,y) of the original image f1(x,y).

$$fus1(x, y) = \frac{\int_{-d}^{d}\int_{-d}^{d} f1(x+x1, y+y1) dx1 dy1}{\int_{-d}^{d}\int_{-d}^{d} dx1 dy1} \quad (36)$$

In the equation (36), "d" indicates the constant for determining the mask size M×M in the smoothing processing.

Step S332:

Subsequently, the high frequency component generation circuit 232 calculates the high frequency component image fh1(x,y) by the equation (37) from the original image f1(x,y)

transferred by the CPU 108 and the image fus1(x,y) after the smoothing processing in the smoothing circuit 231.

$$fh1(x,y)=f1(x,y)-fus1(x,y) \qquad (37)$$

Step S333:

Subsequently, the conversion circuit 233 converts the high frequency component image fh1(x,y) obtained by the high frequency component generation circuit 232, and calculates the converted image fch1(x,y) by equation (38') based on the high frequency component conversion function Ch(x) of FIG. 13.

$$fch1(x,y)=Ch(f1(x,y))\times fh1(x,y) \qquad (38')$$

Step S334:

Subsequently, the main memory 109 as the micro coefficient memory means uses the equation (39) to calculate the micro coefficient c1(x) of the gradation conversion curve F1( ), and stores the coefficient as the table c2(x).

$$c2(x) = 1 / \frac{\partial F1(x)}{\partial x} - 1 \qquad (39)$$

Step S335:

The high frequency component addition circuit 234 adds the converted image fc1h(x,y) in the conversion circuit 233 to the original image f1(x,y). Specifically, the image fad(x,y) after the addition of the high frequency component is calculated by the equation (40).

$$fad(x,y)=f1(x,y)+c2(f1(x,y))\times fch1(x,y) \qquad (40)$$

Step S336:

Subsequently, the gradation conversion circuit 235 performs the gradation conversion processing shown by the equation (41) to the image fad(x,y) obtained by the high frequency component addition circuit 234 to calculate the image fdr2(x,y) after the final DRC processing, using the gradation conversion curve F1( ) shown in FIG. 4.

$$fdr2(x,y)=F1(fad(x,y)) \qquad (41)$$

Step S307:

Thereafter, as described above, the image fdr2(x,y) after the DRC processing obtained by the DRC processing circuit 112*a* is supplied to the gradation conversion circuit 112*c*, subjected to the gradation conversion processing, and subsequently displayed on the screen of the image display 111 or outputted onto the film.

As described above, in the present embodiment, since the high frequency component of the original image before the gradation conversion processing is used to perform the DRC processing, as compared with the DRC processing which uses the high frequency component of the original image after the gradation conversion processing, the DRC processing can be performed using a more precise (less digit drop) high frequency component. In addition to the effect of the first' embodiment, this can provide an effect that a higher frequent component image with a satisfactory restorability can be obtained after the DRC processing.

Additionally, it is needless to say that the object of the present invention is also achieved by providing the system or the apparatus with the memory medium in which the program code of software to realize the functions of the host computer and terminals of the above-described embodiments is stored, and reading and executing the program code stored in the memory medium by the computer (or CPU or MPU) of the system or the apparatus. In this case, the program code itself read from the memory medium realizes the functions of the respective embodiments, and the memory medium in which the program code is stored constitutes the present invention.

Examples of the memory medium for supplying the program code include ROM, floppy disk, hard disk, optical disk, magnetic optical disk, CD-ROM, CD-R, magnetic tape, nonvolatile memory card, and the like.

Moreover, the functions of the respective embodiments are realized by executing the program code read by the computer, but additionally, when the OS or the like operating on the computer performs a part or the whole of the actual processing based on the instruction of the program code, the functions of the above-described embodiments can be realized by the processing. Needless to say, this case is also included in the present invention.

Furthermore, after the program code read from the memory medium is written to the function expansion board inserted to the computer or the memory disposed in the function expansion unit connected to the computer, the CPU or the like disposed in the function expansion board or the function expansion unit performs a part or the whole of the actual processing based on the instruction of the program code, and the functions of the above-described embodiments can also be realized by the processing. Needless to say, this case can also be included.

Although the present invention has been described by some preferable embodiments, it will be understood that the scope of right included in the invention is not limited by the embodiments. On the contrary, the scope of right of the present invention includes all of improvements, modifications, and equivalents included in the scope of the appended claims.

What is claimed is:

1. An image processing apparatus for performing a dynamic range compression processing on an arbitrary image to add a high frequency component obtained based on the image, the image processing apparatus comprising:

conversion means for converting the magnitude of the amplitude of the added high frequency component based on the magnitude of the high frequency component, wherein said conversion means converts the high frequency component in such manner that the increase ratio of the absolute value of the converted high frequency component monotonously increases with the increase of the absolute value of the high frequency component.

2. An image processing method for performing a dynamic range compression processing on an arbitrary image to add a high frequency component obtained based on the image, the image processing method comprising:

a converting step, of converting the magnitude of the amplitude of the added high frequency component based on the pixel value of the arbitrary image, wherein said converting step includes a step of converting the high frequency component in such manner that the increase ratio of the absolute value of the converted high frequency component monotonously increases with the increase of the absolute value of the high frequency component.

* * * * *